United States Patent
Sorensen et al.

(10) Patent No.: US 9,820,885 B2
(45) Date of Patent: Nov. 21, 2017

(54) DUAL BLADE OPHTHALMOLOGIC SURGERY DEVICE

(71) Applicant: Neomedix Corporation, Tustin, CA (US)

(72) Inventors: John T. Sorensen, Lake Elsinore, CA (US); Michael Mittelstein, Laguna Niguel, CA (US); Soheila Mirhashemi, Laguna Niguel, CA (US)

(73) Assignee: NeoMedix Corporation, Tustin, CA (US)

( * ) Notice: Subject to any disclaimer, the term of this patent is extended or adjusted under 35 U.S.C. 154(b) by 0 days.

(21) Appl. No.: 15/076,624

(22) Filed: Mar. 21, 2016

(65) Prior Publication Data

US 2016/0220418 A1  Aug. 4, 2016

Related U.S. Application Data (60) Continuation of application No. 14/789,632, filed on Jul. 1, 2015, now Pat. No. 9,358,155, which is a (Continued)

(51) Int. Cl.
*A61B 17/32* (2006.01)
*A61F 9/007* (2006.01)
(Continued)

(52) U.S. Cl.
CPC .. *A61F 9/00781* (2013.01); *A61B 17/320016* (2013.01); *A61B 18/1482* (2013.01); *A61F 9/007* (2013.01); *A61F 9/0079* (2013.01); *A61F 9/00736* (2013.01); *A61B 2017/320064* (2013.01); *A61B 2018/00083* (2013.01); *A61B 2018/1497* (2013.01)

(58) Field of Classification Search
CPC .... A61F 9/00781; A61F 9/0079; A61F 9/007; A61F 2009/00868; A61F 9/00736–9/00763; A61F 9/013–9/0133; A61B 17/320016; A61B 18/1482; A61B 2018/00083; A61B 2018/1497
USPC ............... 606/167, 107, 166, 170, 184, 185; 600/566–567; 30/304–305, 287
See application file for complete search history.

(56) References Cited

U.S. PATENT DOCUMENTS 421,855 A   2/1890 Burk
637,463 A   11/1899 Hegerty
(Continued)

FOREIGN PATENT DOCUMENTS

EP   0073803 A1   3/1983
EP   1455698 A1   9/2004
(Continued)

OTHER PUBLICATIONS

U.S. Patent Office Action dated Sep. 29, 2009 in related U.S. Appl. No. 10/560,267, filed May 11, 2006.
(Continued)

*Primary Examiner* — Amy R Weisberg
(74) *Attorney, Agent, or Firm* — Robert D. Buyan; Stout, Uxa & Buyan, LLP (57) ABSTRACT

A dual blade device and method useable for performing an ab interno procedure within a human eye to remove a strip of trabecular meshwork tissue.

11 Claims, 3 Drawing Sheets

Related U.S. Application Data continuation of application No. 14/481,754, filed on Sep. 9, 2014, now Pat. No. 9,107,729, which is a division of application No. 13/159,356, filed on Jun. 13, 2011, now abandoned, which is a division of application No. 10/560,267, filed as application No. PCT/US2004/018488 on Jun. 10, 2004, now Pat. No. 7,959,641.

(60) Provisional application No. 60/477,258, filed on Jun. 10, 2003.

(51) Int. Cl.
*A61B 18/14* (2006.01)
*A61B 18/00* (2006.01)

(56) References Cited

U.S. PATENT DOCUMENTS

| | | |
|---|---|---|
| 2,130,949 A | 9/1938 | Collens |
| 2,220,169 A | 11/1940 | Murdock |
| 2,364,333 A | 12/1944 | Wisher |
| 3,294,085 A | 12/1966 | Wallace |
| 3,365,798 A | 1/1968 | Cunningham |
| 3,776,238 A | 12/1973 | Peyman et al. |
| 3,882,872 A | 5/1975 | Douvas et al. |
| 3,972,117 A | 8/1976 | Fogg |
| 4,011,869 A | 3/1977 | Seiler, Jr. |
| 4,111,207 A | 9/1978 | Seiler, Jr. |
| 4,255,854 A | 3/1981 | Bilbao |
| 4,365,957 A | 12/1982 | Das |
| 4,428,748 A | 1/1984 | Peyman et al. |
| 4,472,879 A | 9/1984 | Sizemore |
| 4,501,274 A | 2/1985 | Skjaerpe |
| 4,559,942 A | 12/1985 | Eisenberg |
| 4,577,629 A | 3/1986 | Martinez |
| 4,649,919 A | 3/1987 | Thimsen et al. |
| 4,689,040 A | 8/1987 | Thompson |
| 4,706,669 A | 11/1987 | Schlegel |
| 4,712,546 A | 12/1987 | Noe |
| 4,753,234 A | 6/1988 | Martinez |
| 4,759,746 A | 7/1988 | Straus |
| 4,841,984 A | 6/1989 | Armeniades et al. |
| 4,900,300 A * | 2/1990 | Lee ............ A61B 10/04 604/22 |
| 4,955,883 A | 9/1990 | Nevyas et al. |
| 4,955,887 A | 9/1990 | Zirm |
| 5,019,035 A | 5/1991 | Missirlian et al. |
| 5,042,008 A | 8/1991 | Iwasa et al. |
| 5,112,299 A | 5/1992 | Pascaloff |
| 5,123,904 A | 6/1992 | Shimomura et al. |
| 5,163,433 A | 11/1992 | Kagawa et al. |
| 5,222,959 A | 6/1993 | Anis |
| 5,224,950 A | 7/1993 | Prywes |
| 5,269,782 A | 12/1993 | Sutter |
| 5,284,472 A | 2/1994 | Sussman et al. |
| 5,431,646 A | 7/1995 | Vassiliadis et al. |
| 5,431,671 A | 7/1995 | Nallakrishnan |
| 5,458,596 A | 10/1995 | Lax et al. |
| 5,478,338 A | 12/1995 | Reynard |
| 5,487,747 A | 1/1996 | Stagmann et al. |
| 5,529,580 A | 6/1996 | Kusunoki et al. |
| 5,540,706 A | 7/1996 | Aust et al. |
| 5,540,708 A | 7/1996 | Lim et al. |
| 5,558,637 A | 9/1996 | Allonen et al. |
| 5,569,283 A | 10/1996 | Green et al. |
| 5,681,282 A | 10/1997 | Eggers et al. |
| 5,733,297 A | 3/1998 | Wang |
| 5,755,716 A | 5/1998 | Garito et al. |
| 5,807,277 A | 9/1998 | Swaim |
| 5,817,115 A | 10/1998 | Nigam |
| 5,843,106 A | 12/1998 | Heisler |
| 5,865,831 A | 2/1999 | Cozean et al. |
| 5,885,279 A | 3/1999 | Bretton |
| 5,922,003 A | 7/1999 | Anctil et al. |
| 5,957,881 A | 9/1999 | Peters et al. |
| 5,957,914 A | 9/1999 | Cook et al. |
| 5,964,777 A | 10/1999 | Drucker |
| 6,004,199 A | 12/1999 | Habenicht et al. |
| 6,013,049 A | 1/2000 | Rockley et al. |
| 6,068,629 A | 5/2000 | Haissaguerre |
| 6,213,997 B1 | 4/2001 | Hood et al. |
| 6,217,598 B1 | 4/2001 | Berman et al. |
| 6,241,721 B1 | 6/2001 | Cozean et al. |
| 6,251,103 B1 | 6/2001 | Berlin |
| 6,264,668 B1 | 7/2001 | Prywes |
| 6,283,961 B1 | 9/2001 | Underwood et al. |
| 6,290,699 B1 | 9/2001 | Hall et al. |
| 6,293,957 B1 | 9/2001 | Peters et al. |
| 6,382,974 B1 | 5/2002 | Garfinkel |
| 6,388,043 B1 | 5/2002 | Langer et al. |
| 6,419,684 B1 | 7/2002 | Heisler et al. |
| 6,428,501 B1 | 8/2002 | Reynard |
| 6,428,539 B1 | 8/2002 | Baxter et al. |
| 6,432,104 B1 | 8/2002 | Durgin et al. |
| 6,497,712 B1 | 12/2002 | Feaster |
| RE38,018 E | 3/2003 | Anctil et al. |
| 6,557,258 B1 | 5/2003 | Roberts et al. |
| 6,720,402 B2 | 4/2004 | Langer et al. |
| 6,759,481 B2 | 7/2004 | Tong |
| 6,979,328 B2 | 12/2005 | Baerveldt et al. |
| 7,131,975 B2 | 11/2006 | Adams |
| 7,244,256 B2 | 7/2007 | DeCesare et al. |
| 7,374,566 B1 | 5/2008 | Schossau |
| 7,604,663 B1 | 10/2009 | Reimink et al. |
| 7,632,303 B1 | 12/2009 | Stalker et al. |
| 7,648,591 B2 | 1/2010 | Furst et al. |
| 7,785,321 B2 | 8/2010 | Baerveldt et al. |
| 7,842,034 B2 | 11/2010 | Mittelstein et al. |
| 7,935,131 B2 | 5/2011 | Anthamatten et al. |
| 7,955,387 B2 | 6/2011 | Richter |
| 7,959,641 B2 | 6/2011 | Sorensen et al. |
| 8,038,923 B2 | 10/2011 | Berger et al. |
| 8,069,546 B1 | 12/2011 | Whittemore |
| 8,147,424 B2 | 4/2012 | Kassab et al. |
| 2001/0034932 A1 | 11/2001 | MacDonald |
| 2001/0053873 A1 | 12/2001 | Schaaf et al. |
| 2002/0002372 A1 | 1/2002 | Jahns et al. |
| 2002/0026205 A1 | 2/2002 | Matsutani et al. |
| 2002/0038129 A1 | 3/2002 | Peters et al. |
| 2002/0111608 A1 | 8/2002 | Baerveldt et al. |
| 2003/0208217 A1 | 11/2003 | Dan |
| 2004/0138685 A1 | 7/2004 | Clague et al. |
| 2004/0153111 A1 | 8/2004 | Hosoada |
| 2004/0204732 A1 | 10/2004 | Muchnik |
| 2004/0210245 A1 | 10/2004 | Erickson et al. |
| 2005/0090849 A1 | 4/2005 | Adams |
| 2005/0159767 A1 | 7/2005 | Adams et al. |
| 2006/0095055 A1 | 5/2006 | Douglas et al. |
| 2006/0106370 A1 | 5/2006 | Baerveldt et al. |
| 2006/0149194 A1 | 7/2006 | Conston et al. |
| 2006/0149267 A1 | 7/2006 | Nordt |
| 2006/0200180 A1 | 9/2006 | Lee |
| 2006/0212060 A1 | 9/2006 | Hacker et al. |
| 2006/0241580 A1* | 10/2006 | Mittelstein ......... A61B 18/1482 606/41 |
| 2007/0010812 A1 | 1/2007 | Mittelstein et al. |
| 2007/0073275 A1 | 3/2007 | Conston et al. |
| 2007/0149974 A1 | 6/2007 | Mangione |
| 2007/0276420 A1 | 11/2007 | Sorensen et al. |
| 2008/0077146 A1 | 3/2008 | Pernsteiner et al. |
| 2009/0248141 A1 | 10/2009 | Shandas et al. |
| 2009/0287233 A1 | 11/2009 | Huculak |
| 2011/0077626 A1 | 3/2011 | Baerveldt et al. |
| 2011/0230877 A1 | 9/2011 | Huculak et al. |
| 2012/0083727 A1 | 4/2012 | Barnett |
| 2012/0123533 A1 | 5/2012 | Shiuey |
| 2012/0191120 A1 | 7/2012 | Linsi |
| 2015/0045820 A1 | 2/2015 | Kahook |

FOREIGN PATENT DOCUMENTS

| | | |
|---|---|---|
| EP | 1615604 A1 | 1/2006 |
| EP | 2303203 A1 | 4/2011 |

(56) References Cited

FOREIGN PATENT DOCUMENTS

| | | |
|---|---|---|
| JP | 46-25677 Y1 | 9/1971 |
| KR | 1020040058309 A | 3/2004 |
| WO | WO 91/17793 A1 | 11/1991 |
| WO | WO 98/27876 A | 7/1998 |
| WO | WO2001/078631 A2 | 10/2001 |
| WO | WO 02/056805 A | 7/2002 |
| WO | WO2003/045290 A1 | 6/2003 |
| WO | WO2004/093761 A1 | 11/2004 |
| WO | WO2004/110501 A2 | 12/2004 |
| WO | WO2009/140185 A1 | 11/2009 |
| WO | WO 2011/030081 A1 | 3/2011 |
| WO | WO2013/163034 A1 | 10/2013 |

OTHER PUBLICATIONS

U.S. Patent Office Action dated Mar. 12, 2010 in related U.S. Appl. No. 10/560,267, filed May 11, 2006.
Jacobi, Philipp C. et al. "Technique of Goniocurellage: A Potential Treatment for Advanced Chronic Open Angle Glaucoma," British Journal of Ophthalmology, 1997; 81, pp. 302-307.
Soohoo, Jeffrey R., et al. "Ab Interno Trabeculectomy in the Adult Patient," Middle East African Journal of Ophthalmology, vol. 22, No. 1, Jan.-Mar. 2015, pp. 25-29.
Ting, J. L. M. et al., (2012) "Ab interno trabeculectomy: Outcomes in exfoliation versus primary open-angle glaucoma," J Cataract. Refract. Surg. 38(2),315-323.
Francis, B. A. et al., (2006) "Ab interno trabeculectomy: development of a novel device (Trabectome) and surgery for open-angle glaucoma," J Glaucoma 15(1), 68-73.
Minckler, D. S. et al., (2005) "Clinical Results with the Trabectome for Treatment of Open-Angle Glaucoma," Opthalmology 112(6), 962-967.
Tan, Yar-Li, et al., "Postoperative Complications after Glaucoma Surgery for Primary Angle-Closure Glaucoma vs Primary Open-Angle Glaucoma," Arch Ophthalmol. 2011; 129(8), pp. 987-992.
Johnson, Douglas H. et al., "Human Trabecular Meshwork Organ Culture. A New Method." Invest. Ophthalmol. Vis. Sci. 28(6),945-953.
Quigley, H. A. and Broman, A. T., (2006) "The number of people with glaucoma worldwide in 2010 and 2020," Br. J Ophthalmol. 90(3),262-267.
Jacobi, P. C. et al., (1999) "Goniocurettage for removing trabecular meshwork: clinical results of a new surgical technique in advanced chronic open-angle glaucoma," Am. J Ophthalmol. 127(5),505-510.
Pantcheva, M. B. and Kahook, M. Y., (2010) "Ab Interno Trabeculectomy," Middle East African Journal of Ophthalmology 17(4), 287-289.
Seibold, L. K. et al., (2013) "Preclinical Investigation of Ab Interno Trabeculectomy Using a Novel Dual-Blade Device," Am. J Ophthalmol. 155(3), 524-529.e522.
Anderson, D.R., (1983) "Trabeculotomy compared to goniotomy for glaucoma in children," Ophthalmology 90(7),805-806.
Grant, W., (1963) "Experimental aqueous perfusion in enucleated human eyes," Arch.Ophthalmol. 69(6), 783-801.
Grant, W. M., (1951) "Clinical measurements of aqueous outflow," AMA Archives of Ophthalmology 46(2), 113-131.
Herschler, J. and Davis, E. B., (1980) "Modified goniotomy for inflammatory glaucoma. Histologic evidence for the mechanism of pressure reduction," Arch. Ophthalmol. 98(4), 684-687.
Jea, S. Y. et al., (2012) "Ab Interno Trabeculectomy Versus Trabeculectomy for Open Angle Glaucoma," Ophthalmology 119(1), 36-42.
Luntz, M. H. and Livingston, D. G., (1977) "Trabeculotomy ab externo and trabeculectomy in congenital and adult-onset glaucoma," Am. J Ophthalmol. 83(2), 174-179.
Dominguez, A., "Ab Interno Trabeculotomy," Bulletins et memoires de la Societe francaise, vol. 86, 1973. Abstract.
Skjaerpe, F., "Selective Trabeculectomy. A Report of a New Surgical Method for Open Angle Glaucoma," ACTA Ophthalmologica, vol. 61, pp. 714-727, 1983.

\* cited by examiner

DUAL BLADE OPHTHALMOLOGIC SURGERY DEVICE

RELATED APPLICATIONS

This application is a continuation of U.S. patent application Ser. No. 14/789,632 filed Jul. 1, 2015 and issued as U.S. Pat. No. 9,358,155 issued on Jun. 7, 2016, which is a continuation of U.S. patent application Ser. No. 14/481,754 filed Sep. 9, 2014 and issued as U.S. Pat. No. 9,107,729 on Aug. 18, 2015, which is a division of U.S. patent application Ser. No. 13/159,356 filed Jun. 13, 2011 and now abandoned, which is a division of U.S. patent application Ser. No. 10/560,267 filed May 11, 2006 and issued as U.S. Pat. No. 7,959,641 on Jun. 14, 2011, which is a 35 U.S.C. §371 national stage of PCT International Patent Application No. PCT/US2004/018488 filed Jun. 10, 2004, which claims priority to U.S. Provisional Patent Application No. 60/477,258 filed on Jun. 10, 2003, the entire disclosure of each such prior patent and application being expressly incorporated herein by reference.

BACKGROUND OF THE INVENTION

There are numerous medical and surgical procedures in which it is desirable to cut and remove a strip of tissue of controlled width from the body of a human or veterinary patient. For example, it may sometimes be desirable to form an incision of a controlled width (e.g., an incision that is wider than an incision made by a typical scalpel or cutting blade) in the skin, mucous membrane, tumor, organ or other tissue or a human or animal. Also, it may sometimes desirable to remove a strip or quantity of tissue from the body of a human or animal for use as a biopsy specimen, for chemical/biological analysis, for retention or archival of DNA identification purposes, etc. Also, some surgical procedures require removal of a strip of tissue of a known width from an anatomical location within the body of a patient.

One surgical procedure wherein a strip of tissue of a known width is removed from an anatomical location within the body of a patient is an ophthalmological procedure used to treat glaucoma. This ophthalmological procedure is sometimes referred to as a goniectomy. In a goniectomy procedure, a device that is operative to cut or ablate a strip of tissue of approximately 2-10 mm in length and about 50-200 µm in width is inserted into the anterior chamber of the eye and used to remove a full thickness strip of tissue from the trabecular meshwork. The trabecular meshwork is a loosely organized, porous network of tissue that overlies a collecting canal known as Schlemm's canal. A fluid, known as aqueous humor, is continually produced in the anterior chamber of the eye. In normal individuals, aqueous humor flows through the trabecular meshwork, into Shlemm's Canal and out of the eye through a series of ducts. In patients who suffer from glaucoma, the drainage of aqueous humor from the eye may be impaired by elevated flow resistance through the trabecular meshwork, thereby resulting in an increase in intraocular pressure. The goniectomy procedure can restore normal drainage of aqueous humor from the eye by removing a full thickness segment of the trabecular meshwork, thus allowing the aqueous humor to drain through the open area from which the strip of trabecular meshwork has been removed. The goniectomy procedure and certain prior art instruments useable to perform such procedure are described in U.S. patent application Ser. No. 10/052,473 published as No. 2002/011608A1 (Baerveldt), the entirety of which is expressly incorporated herein by reference.

At present there remains a need in the art for the development of simple, inexpensive and accurate instruments useable to perform the goniectomy procedure as well as other procedures where it is desired to remove a strip of tissue from a larger mass of tissue.

SUMMARY OF THE INVENTION

The present invention provides a device for cutting a strip of tissue of approximate width W from a mass of tissue. The device generally comprises a) an elongate cutting tube that has a distal end and a lumen that opens through an opening in the distal end and b) first and second cutting edges formed on generally opposite edges of the distal end of the cutting tube and separated by a distance D. The cutting tube is advanceable through tissue such that the first and second cutting edges will cut a strip of tissue having approximate width W, wherein the approximate width W is approximately equal to the distance D between the first and second cutting edges. In some embodiments, the strip of tissue may be aspirated or otherwise removed through the lumen of the cutter tube. In some embodiments, the device may include apparatus useable to sever (e.g., transversely cut or transect) the strip of tissue when the strip of tissue has reached a desired length.

Further in accordance with the invention there is provided a method for cutting a strip of tissue of width W from a tissue mass. This method generally comprises the steps of a) providing a device that comprises i) an elongate cutting tube that has a distal end and a lumen that opens through an opening in the distal end and ii) first and second cutting edges formed on generally opposite edges of the distal end of the cutting tube and separated by a distance D that is approximately equal to the width W of the strip of tissue to be cut; and b) advancing the distal end of the cutting tube through the mass of tissue such that the first and second cutting edges cut a strip of tissue of approximate width W. Further aspects and elements of the invention will be understood by those of skill in the art upon reading the detailed description of specific examples set forth herebelow.

DETAILED DESCRIPTION

The following detailed description, and the drawings to which it refers, are provided for the purpose of describing and illustrating certain preferred embodiments or examples of the invention only, and no attempt has been made to exhaustively describe all possible embodiments or examples of the invention. Thus, the following detailed description and the accompanying drawings shall not be construed to limit, in any way, the scope of the claims recited in this patent application and any patent(s) issuing therefrom.

One example of a needle cutter device 10 of the present invention is shown in FIGS. 1-4. This needle cutter device 10 generally comprises an elongate cutting tube 14 that has a distal end and a lumen 27 that opens through an opening in the distal end. First and second cutting edges 20, 22 are formed on generally opposite edges of the distal end of the cutting tube 14. These first and second cutting edges 20, 22 are separated by a distance D, as shown in the distal end view of FIG. 3B. In the particular example shown in the drawings, the first and second cutting edges 20, 22 are located on opposite lateral sides of the distal end of the cutting tube 14 and a blunt, protruding tip 24 is located on the bottom of the distal end of the culling tube. Also, a blunt edge 26 is located at the top of the distal end of the cutting tube 14. Thus, only the lateral cutting edges 20, 22 are sharp and intended to cut tissue. The blunt, protruding tip 24 can, in some applications, be configured and used to facilitate insertion of the device 10 to its intended location and/or the blunt protruding tip 24 may be placed in an anatomical or man made grove or channel (e.g., Schlemm's Canal of the eye) such that it will then advance through the channel or groove and guide the advancement and positioning of the remainder of the device 10.

Figure 6:
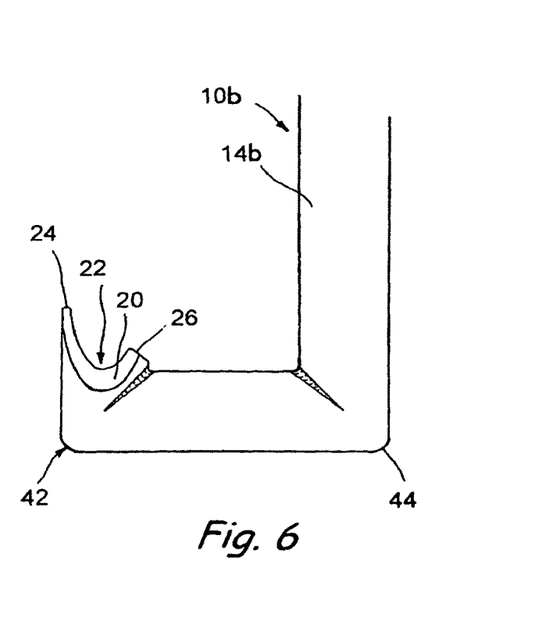
FIG. 6 is a side view of the distal portion of another embodiment of a needle cutter device of the present invention having a plurality of curves or bends formed in the cutting tube.

One or more bends or curves may optionally be formed in the cutting tube 14 to facilitate its use for its intended purpose. For example, in the embodiment of the device 10 shown in FIG. 2, a single bend 17 of approximately 90 is formed near the distal end of the cutting tube 14. In the embodiment of the device 10b shown in FIG. 6, two separate bends of approximately 90 degrees each are formed at spaced apart locations on the cutting tube 14, thereby giving the cutting tube 14 a generally U shaped configuration. It will be appreciated that any number of bends or curves, in any direction and of any severity may be formed in the cutting tube 14 to facilitate its use in specific procedures or to enable it to be inserted through tortuous anatomical channels of the body. In most cases, the degree of curvature in embodiments where a single bend or curve is formed will be between approximately 30 and approximately 90 degrees and in embodiments where more than one bend or curve are formed in the cutting tube 14 each such bend or curve will typically be between approximately 15 to approximately 90 degrees.

Figure 4:
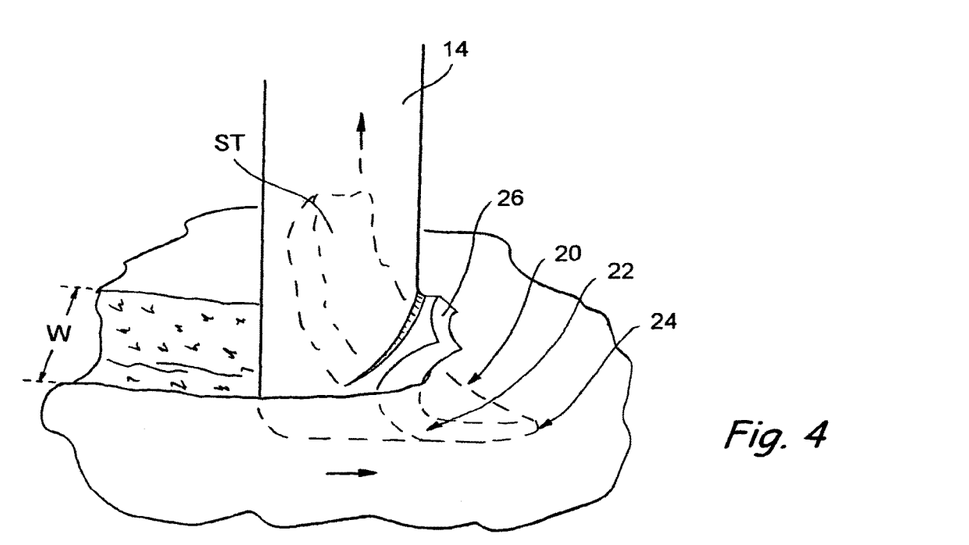
FIG. 4 is a side view of a distal portion of a needle cutter device of the present invention being used to cut a strip of tissue of approximate width W.

As shown in FIG. 4, when the cutting tube 14 is advanced through tissue, distal end first, the first and second cutting edges 20, 22 will cut a strip ST of tissue having approximate width W, such approximate width W being approximately equal to the distance D between the first and second cutting edges 20, 22. The severed strip ST of tissue will enter the lumen 27 of the cutting tube 14 as the device advances. Negative pressure may be applied to lumen 27 to aspirate the strip ST of tissue and/or fluid and/or other matter through lumen 27.

The device 10 may optionally include a second lumen. Such second lumen may be used for infusion of fluid through the device 10 or for other purposes. In the embodiment shown in FIGS. 1 and 2, the device 10 comprises an outer tube 16 in addition to the cutting tube 14. The cutting tube 14 is of smaller diameter than the outer tube 16 and the cutting tube 14 may extend through the lumen 19 of the outer tube 16 such that a distal portion of the cutting tube 14 extends out of and beyond the distal end of the outer tube 16, as may be seen in FIG. 2. The distal end of the outer tube 16 is tapered and in close approximation with the outer surface of the cutting tube 14. Fluid may be infused through the lumen 19 of the outer tube 16, through the space between the outer surface of the cutting tube 14 and the inner surface of the outer tube 16. Fluid that is infused through the lumen 19 of the outer tube 16 may flow out of one or more apertures 11 formed near the distal end of the outer tube.

Figure 5:
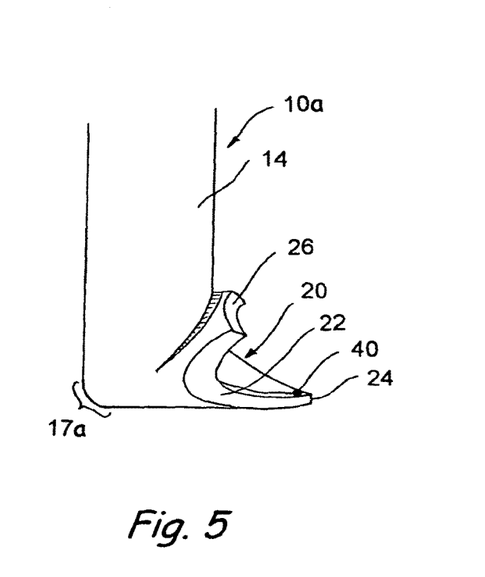
FIG. 5 is a perspective view of the distal portion of a needle cuter device of the present invention incorporating apparatus for severing a strip of tissue cut by the needle cutter device after the strip of tissue has reached a desired length.

In some embodiments, the device 10 may be equipped with severing apparatus for severing (e.g., transversely cutting or transecting) the strip ST of tissue to fully excise or detach the strip ST of tissue from the remaining tissue mass and/or from the body of a human or animal subject. Such severing apparatus may comprise any suitable type of tissue cutter such as a blade, scissor, guillotine, electrode(s), laser, energy emitting tissue cutter, mechanical tissue cutter, etc. FIG. 5 shows an example of an embodiment of the device 10a wherein monopolar or bipolar electrode(s) 40 are located on the distal end of the cutting tube 14. When it is desired to sever the strip ST of tissue, the electrode(s) is/are energized with sufficient energy to sever the strip ST, thereby disconnecting the strip ST from the remaining tissue mass and/or the body of the human or animal subject.

In some embodiments of the device 10, the cutting edges 20, 22 may be heated such that they will cauterize as the cut. As those of skill in the art will appreciate, such heating of the cutting edges 20, 22 may be accomplished by placement of electrode(s) near the cutting edges 20, 22 such that, when the electrode(s) is/are energized, the cutting edges 20, 22 will become heated to a temperature suitable for the desired cauterization function.

Figure 1:
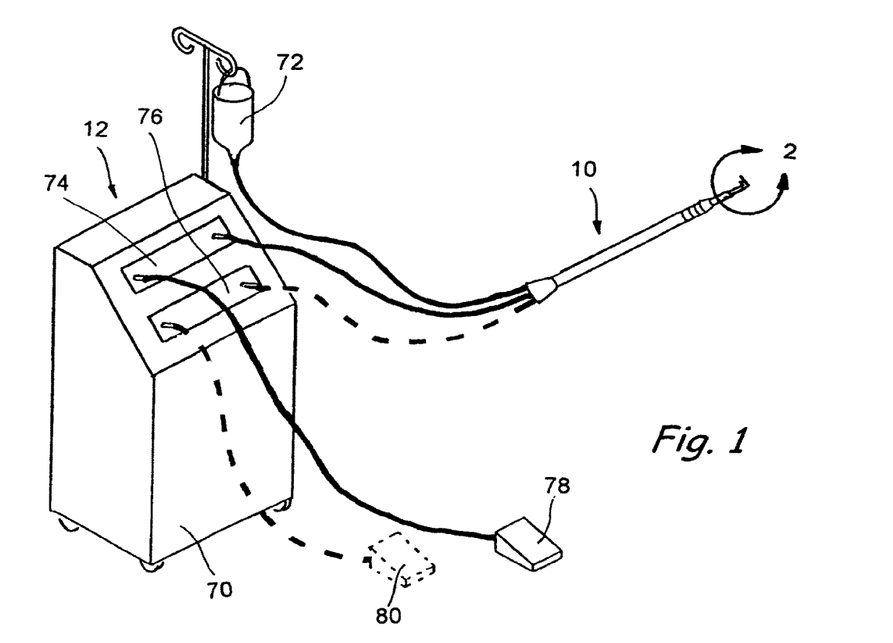
FIG. 1 is a perspective view of a system incorporating a needle cutting device of the present invention.
Figure 2:
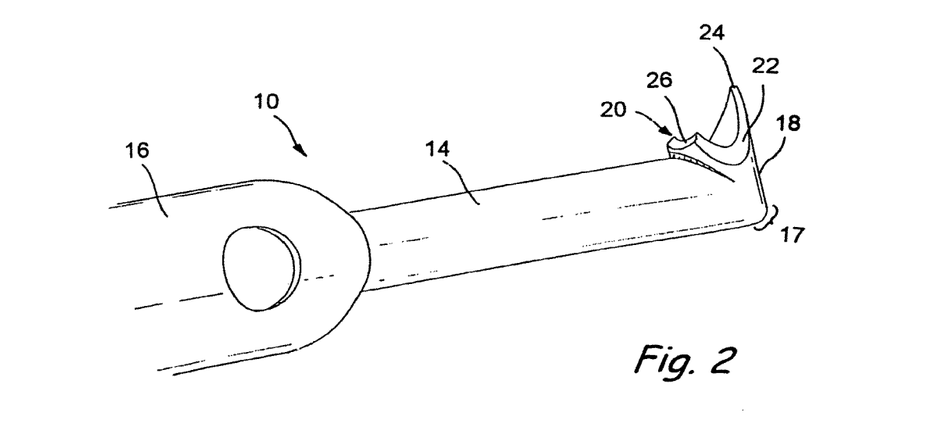
FIG. 2 is an enlarged perspective view of section 2 of FIG. 1.
Figure 3A:
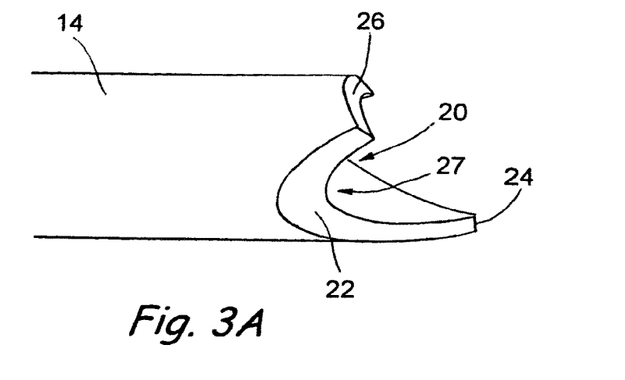
FIGS. 3A-3D show various steps in a method for manufacturing a needle cutter of the present invention.
Figure 3B:
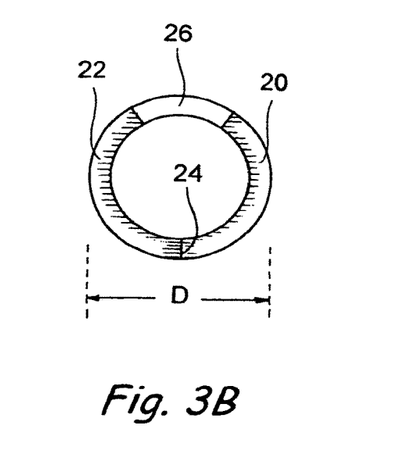
Figure 3C:
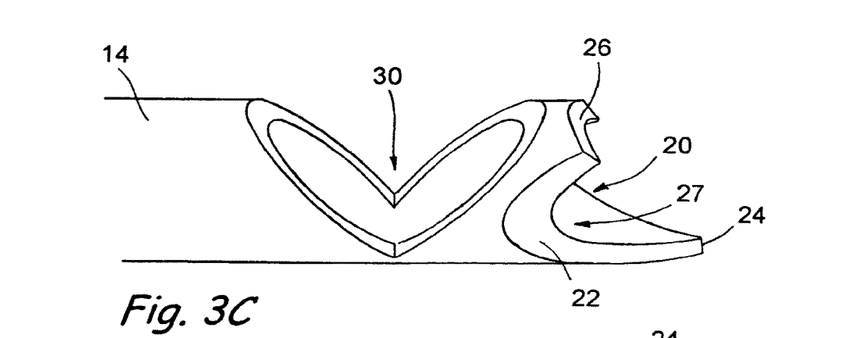
Figure 3D:
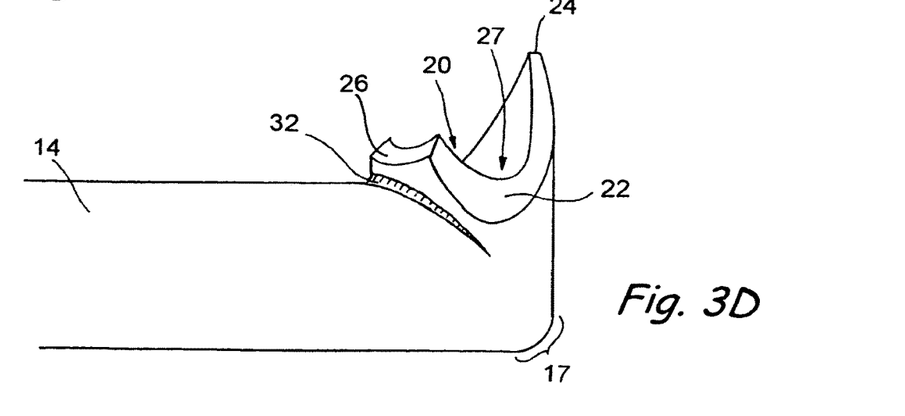

The needle cutter device 10 of the present invention may optionally be used as part of a system 12, as shown in FIG. 1. The basic components of the system 12 comprise an aspiration pump module 74 and a source of irrigation fluid 72, mounted on a surgical roller cart 70. Control of the console functions during procedures may be accomplished by an aspiration foot pedal 78 which controls an aspiration pump 74 and variation in the height of the source of infusion fluid 72 to change the gravity fed pressure or flow rate of infusion fluid through the device. A pinch valve, or other means, may also be incorporated in the console to control flow of the irrigation fluid to the needle cutter device 10. In embodiments that include apparatus (e.g., electrode(s)) for heating the cutting edges 20, 22 and/or for severing the strip ST of tissue (FIG. 5), the system 11 may additionally comprise an electrical current source, such as an electrosurgical generator 76 and electrosurgical foot pedal 80 which controls the electrosurgical generator to deliver desired amount(s) of energy to the electrode(s) or other electrical elements (e.g., resistance heater(s), etc.) on the device 10. As an option, all of the basic control functions of system 12 may be integrated into a single footpedal to facilitate use.

The device 10 may be provided as a pre-sterilized, single-use disposable probe or tip that is attachable to a standard surgical irrigation/aspiration handpiece such as that commercially available as The Rhein I/A Tip System from Rhein Medical, Inc., Tampa, Fla. After the device 10 has been attached to the handpiece, it may be connected to any or all of the electrosurgical generator module 76, aspiration pump module 74 and the source of irrigation fluid 72, as shown. Thus, the device 10 may be fully equipped for irrigation, aspiration, and electrosurgical capabilities, as described herein.

FIGS. 3A-3D show an example of a method for manufacturing the cutting tube 14 from standard tubing (e.g., stainless steel hypodermic tubing). Initially, the distal end of a tube is cut to form the lateral cutting edges 20, 22, the protruding tip 24 and the blunt top edge 26. Thereafter, if it is desired to have one or more bends or curves in the cutting tube 14, angular cut out(s) 30 may be formed in the tube 14, as shown in FIG. 30. Thereafter, the tube 14 is bent to bring the edges of each angular cut out 30 into apposition and weld, adhesive or other joining techniques are used to weld or join the apposed edges of the cut outs together, thereby forming the desired bend(s) or curve(s) in the cutting tube 14. Likewise, if it is desired to have one or more bends or curves in the cutting tube 14, the tube 14 may be directly bent to form said curves or bends without the use of angular cut outs(s) 30. It may be appreciated that the use of angular cut-out(s) 30 allow a tube 10 of a given diameter to incorporate a curve or angle in a more compact form than is possible by bending tubing 10 of a given diameter to said curve or angle without kinking or damaging tube 10.

The device 10 and system 12 are useable to perform a variety of procedures wherein it is desired to form an incision or opening of a desired width or to remove, from a mass of tissue, a strip ST of tissue of a desired width.

One particular procedure that may be performed to treat glaucoma, using the device 10 and system 12 of the present invention, is a goniectomy. As explained herein a goniectomy procedure is an ab interno surgical procedure wherein a sector of the trabecular meshwork is removed from the eye of the patient to facilitate drainage of aqueous humor from the anterior chamber of the eye through Schlemm's Canal and the associated collector channels, thereby relieving elevated intraocular pressure.

To perform a goniectomy procedure using the device 10, first a small incision is made in the cornea at about 3 o'clock in the left eye, or at about 9 o'clock in the right eye. A 1.5 mm slit knife may be used to make this incision.

The device 10 is attached to the source of irrigation fluid 72 (e.g., basic balanced salt solution) such that irrigation fluid will flow through lumen 19 of the outer tube 16 and out of outflow aperture 11. The device 10 is then inserted through the incision and into the anterior chamber of the eye (with irrigation flowing). In some cases, during the insertion of the device 10, the source of irrigation fluid 72 may initially connected to the device such that the irrigation fluid will flow through the lumen 27 of the cutter tube 14. In this manner, irrigation fluid will begin to infuse into the anterior chamber of the eye as soon as the distal end of the cutter tube 14 has entered the anterior chamber, rather than being delayed until the larger outer tube 16 and aperture 11 have been advanced through the incision and into the anterior chamber. By this alternative approach, irrigation fluid may be caused to flow out of the distal end of the cutter tube 14 as the device 10 is being inserted, thereby spreading or opening the incision by hydraulic force while in addition increasing the fluid pressure in the anterior chamber. Such spreading or opening of the incision may facilitate advancement of the larger diameter outer tube 16 through the incision. Pressurizing the fluid in the anterior chamber causes the anterior chamber to deepen and may facilitate maneuvering of device 10 within the anterior chamber. In cases where this alternative approach is used, the source of infusion fluid 72 may be disconnected from lumen 27 of the cutter tube 14 after the device 10 has been inserted into the anterior chamber and, thereafter, the infusion fluid source 72 may be reconnected to lumen 19 of outer tube 16 such that infusion fluid will flow out of aperture 11. Negative pressure (e.g., via aspiration pump module 74) may then be applied to lumen 27 of the cutter tube 14 so as to aspirate fluid and debris through lumen 27 as shown in FIG. 4. The vertical height of the infusion fluid source 72 may be adjusted to provide sufficient gravity feed of infusion fluid to make up for the volume of fluid or matter being aspirated from the anterior chamber through lumen 27, thereby maintaining the desired pressure of fluid within the anterior chamber during the procedure.

A lens device (e.g., Ocular Swan-Jacob Autoclavable Gonioprism, Model OSJAG, Ocular Instruments Inc., Bellevue, Wash.) may be positioned on the anterior aspect of the eye to enable the physician to clearly visualize the angle of the eye where the segment of trabecular meshwork is to be removed. Under direct visualization, the device 10 is advanced until the distal tip of the cutter tube 14 is positioned adjacent to the trabecular meshwork at the location where the strip ST is to be removed. Thereafter, the protruding tip 24 is advanced through the trabecular meshwork and into Schlemm's Canal.

The device 10 is then advanced along Schlemm's Canal, thereby causing the cutting edges 20, 22 to cut a strip of the trabecular meshwork, thereby creating an opening through which aqueous humor may drain from the anterior chamber of the eye.

After a strip of tissue of the desired length (e.g., about 2-10 mm) has been cut by the lateral cutting edges 20, 22, any optional tissue severing apparatus (e.g., electrode(S) 40 may be used (if present) to transect or sever the strip ST of tissue thereby disconnecting it from the patient's body and allowing it to be aspirated or drawn into or through lumen 27.

Thereafter, the aspiration is stopped, the device 10 is removed from the eye, and the infusion is stopped.

Following completion of the surgery, aqueous humor will drain from the anterior chamber through the opening that was created by removal of the strip of tissue from the trabecular meshwork TM.

Although the invention has been described above with respect to certain embodiments and examples, it is to be appreciated that such embodiments and examples are non-limiting and are not purported to define all embodiments and examples of the invention. Indeed, those of skill in the art will recognize that various modifications may be made to the above-described embodiments and examples without departing from the intended spirit and scope of the invention and it is intended that all such modifications be included within the scope of the following claims.

What is claimed is:

1. A method for cutting a strip of trabecular meshwork tissue within an eye of a subject, said eye having an anterior chamber, trabecular meshwork tissue and a Schlemm's canal, said method comprising:

a) providing or obtaining a device which comprises;
   an elongate probe that extends along a longitudinal axis;
   a tip which extends laterally from an end of the probe, said tip comprising a platform which has a top surface, a bottom surface, a right side edge, a left side edge and a terminal end, the terminal end being configured to penetrate through trabecular meshwork tissue;
   the tip having a transverse width from the right side edge to the left side edge, said transverse width being narrowest at the terminal end; and
   first and second spaced-apart cutting edges positioned on the device so as to cut tissue that passes along the top surface of the tip and into contact with the cutting edges;

b) inserting the probe into the anterior chamber of the eye;
c) advancing the tip through trabecular meshwork tissue and into the Schlemm's Canal of the eye such that trabecular meshwork tissue is in contact with the top surface;
d) moving the probe to cause the tip to advance through the Schlemm's Canal such that trabecular meshwork tissue moves along the top surface of the tip and into contact with the first and second spaced-apart cutting edges, thereby cutting a strip of the trabecular meshwork tissue.

2. A method according to claim 1 further comprising the step of keeping the anterior chamber filled.

3. A method according to claim 2 wherein the device further comprises an infusion lumen and wherein fluid is infused through the infusion lumen to keep the anterior chamber filled.

4. A method according to claim 3 wherein step a comprises:
forming an incision in the eye;
causing fluid to flow out of the infusion lumen and into the incision, thereby spreading or opening the incision; and
thereafter inserting the probe through the incision and into the anterior chamber of the eye.

5. A method according to claim 3 wherein the device further comprises an aspiration lumen and the method further comprises aspirating fluid through the aspiration lumen.

6. A method according to claim 1 wherein the strip of trabecular meshwork tissue cut in step d has a length of about 2 to 10 millimeters.

7. A method according to claim 1 wherein, after cutting of the strip of trabecular meshwork tissue in step d, the strip of trabecular meshwork tissue remains connected to the eye and wherein the method further comprises the step of disconnecting the strip of strip of trabecular meshwork tissue from the eye.

8. A method according to claim 7 wherein the step of disconnecting the strip of trabecular meshwork tissue from the eye comprises using a tissue disconnecting apparatus to disconnect the strip of trabecular meshwork tissue from the eye.

9. A method according to claim 1 wherein the method is performed under direct visualization through a lens device positioned on an anterior aspect of the eye.

10. A method according to claim 1 wherein the tip extends laterally from said end of the probe at an angle of between approximately 30 and approximately 90 degrees relative to the longitudinal axis of the probe and wherein step d comprises moving the distal end of the probe laterally such that the tip advances through Schlemm's Canal.

11. A method according to claim 1 wherein a curve is formed in the elongate probe proximal to the end of the probe from which the tip laterally extends.

\* \* \* \* \*

(12) INTER PARTES REVIEW CERTIFICATE (2949th)
United States Patent
Sorensen et al.

(10) Number: US 9,820,885 K1
(45) Certificate Issued: Dec. 22, 2022

(54) DUAL BLADE OPTHALMOLOGIC SURGERY DEVICE (71) Applicants: John T. Sorensen; Michael Mittelstein; Soheila Mirhashemi (72) Inventors: John T. Sorensen; Michael Mittelstein; Soheila Mirhashemi (73) Assignee: MICROSURGICAL TECHNOLOGY, INC.

Trial Number:

IPR2021-00017 filed Oct. 2, 2020

Inter Partes Review Certificate for:

Patent No.: 9,820,885
Issued: Nov. 21, 2017
Appl. No.: 15/076,624
Filed: Mar. 21, 2016

The results of IPR2021-00017 are reflected in this inter partes review certificate under 35 U.S.C. 318(b).

INTER PARTES REVIEW CERTIFICATE
U.S. Patent 9,820,885 K1
Trial No. IPR2021-00017
Certificate Issued Dec. 22, 2022

AS A RESULT OF THE INTER PARTES REVIEW PROCEEDING, IT HAS BEEN DETERMINED THAT:

Claims 1-11 are cancelled.

\* \* \* \* \*